US008101816B2

(12) United States Patent
Arber

(10) Patent No.: US 8,101,816 B2
(45) Date of Patent: Jan. 24, 2012

(54) RGMC MODIFIED TRANSGENIC ANIMALS

(75) Inventor: Silvia Arber, Basel (CH)

(73) Assignee: Novartis Forschungsstiftung, Zweigniederalassung Friedrich Miescher Institute for Biomedical Research, Basel (CH)

( * ) Notice: Subject to any disclaimer, the term of this patent is extended or adjusted under 35 U.S.C. 154(b) by 1020 days.

(21) Appl. No.: 11/572,561

(22) PCT Filed: Jul. 22, 2005

(86) PCT No.: PCT/EP2005/008041
§ 371 (c)(1),
(2), (4) Date: Jan. 10, 2008

(87) PCT Pub. No.: WO2006/008182
PCT Pub. Date: Jan. 26, 2006

(65) Prior Publication Data
US 2008/0196114 A1    Aug. 14, 2008

Related U.S. Application Data

(60) Provisional application No. 60/590,542, filed on Jul. 23, 2004.

(51) Int. Cl.
*A01K 67/027* (2006.01)
*A01K 67/033* (2006.01)

(52) U.S. Cl. .................. 800/18; 800/8; 800/21; 800/25

(58) Field of Classification Search .................... 800/18, 800/8, 21, 25
See application file for complete search history.

(56) References Cited

PUBLICATIONS

Huang et al., A mouse model of juvenile hemochromatosis J Clin Invest. Aug. 1, 2005; 115(8): 2187-2191.*
Levy et al., The C282Y Mutation Causing Hereditary Hemochromatosis Does Not Produce a Null Allele Blood, vol. 94 No. 1 (Jul. 1, 1999): pp. 9-11.*
Sanders Williamset al., Transgenic animals in integrative biology: approaches and interpretations of outcome. Appl Physiol 88: 1119-1126, 2000.*
Moreadith RW,Gene targeting in embryonic stem cells: the new physiology and metabolism. J Mol Med. Mar. 1997;75(3):208-16.*
Keefer, Production of bioproducts through the use of transgenic animal models. Anim Reprod Sci. Jul. 2004;82-83:5-12. Review.*
Sigmund. Viewpoint: are studies in genetically altered mice out of control? Arterioscler Thromb Vasc Biol. Jun. 2000;20(6):1425-9. Review.*
Gerlai R. Gene-targeting studies of mammalian behavior: is it the mutation or the background genotype? Trends Neurosci. May 1996:19(5):177-81.*
Zhang et al.,Evidence That Inhibition of Hemojuvelin Shedding in Response to Iron Is Mediated through Neogenin JBC pp. 12547-12556, 2007.*
Capecchi MR. Altering the genome by homologous recombination. Science. Jun. 16, 1989;244(4910):1288-92. Review.*
Monnier, et al., "RGM is a repulsive guidance molecule for retinal axons", Nature, Sep. 26, 2002, vol. 419, pp. 392-395, Nature Publishing Group (2002).
Niederkofler, et al., "Repulsive Guidance Molecule (RGM) . . . Retinal Topography in the Mouse Visual System", The Jounal of Neuroscience, pp. 808-818, Jan. 28, 2004.
Papanikolaou, et al., "Mutations in HFE2 cause iron overload in chromosome 1q-linked juvenile hemochromatosis", Nature Genetics, vol. 36, No. 1, pp. 77-82, Jan. 2004.
Arber, et al., "Requirement for the Homeobox Gene Hb9 in the Consolidation of Motor Neuron Identity", Neuron, vol. 23, 659-674, Cell Press, Aug. 1999.
Evans, et al., "Establishment in culture of pluripotential cells from mouse embryos", Nature, vol. 292, pp. 154-156, Jul. 9, 1981.
Bradley, et al., "Formation of germ-line chimaeras from embryo-derived teratocarcinoma cell lines", Nature, vol. 309, pp. 255-256, May 17, 1984.
Gossler, et al., "Transgenesis by means of Blastocyst-Derived Embryonic Stem Cell Lines", PNAS, vol. 83, pp. 9065-9069, Dec. 1986.
Robertson, et al., "Germ-line transmission of genes introduced into cultured pluripotential cells by retroviral vector", Nature, vol. 323, pp, 445-448, Oct. 2, 1986.
Wood, et al., "Simple and Efficeint Production of Embryonic Stem Cell-Embryo Chimeras by Coculture", PNAS, vol. 90, pp. 4582-4585, May 1993.
Jaenish, Rudolf, "Transgenic Animals", Science, vol. 240, pp. 1468-1474, Jun. 10, 1998.
Thomas et al., "Site-Directed Mutagenesis by Gene Targeting in Mouse Embryo-Derived Stem Cells", Cell, vol. 51, pp. 503-512, Cell Press, Nov. 6, 1987.
Frohman et al., "Cut, Paste, and Save: New Approaches to Altering Specific Genes in Mice", Cell, vol. 56, pp. 145-147, Cell Press, Jan. 27, 1989.
Capecchi, Mario, "The New Mouse Genetics: Altering the Genome by Gene Targeting", TIG, vol. 5, No. 3, pp. 70-76, Elsevier Science Publishers Ltd, Mar. 1989.
Baribault, Helene, "Embryonic Stem Cell Culture and Gene Targeting in Transgenic Mice", Mol. Biol. Med. vol. 6, pp. 481-492, Academic Press Limited, (1989).
Wagner, Erwin F., "EMBO Medal Review on transferring genes into stem cells and mice", The EMBO Journal, vol. 9, No. 10, pp. 3025-3032, Oxford University Press (1990).
Pietrangelo, Antonello, "Hereditary Hemochromatosis—A New Look at an Old Disease", N. Engl. J. Med. vol. 350, No. 23, Jun. 3, 2004.
Hentze et al., "Balancing Acts: Molecular Control of Mammalian Iron Metabolism", Cell, vol. 117, pp. 285-297, Cell Press, Apr. 30, 2004.

\* cited by examiner

*Primary Examiner* — Maria Leavitt
(74) *Attorney, Agent, or Firm* — Hoxie & Associates LLC

(57) ABSTRACT

The invention provides a new reproducible transgenic mouse model for the study of iron accumulation in the body. In particular, the invention concerns the study of iron overload in an RGMc knockout mouse model and its use in drug discovery and research.

3 Claims, 4 Drawing Sheets

RGMC MODIFIED TRANSGENIC ANIMALS

This application is the National Stage of Application No. PCT/EP05/008041, filed on Jul. 22, 2005, which claims benefit under 35 U.S.C. §119(e) of U.S. Provisional Application No. 60/590,542, filed Jul. 23, 2004. The contents of both are incorporated herein by reference in their entirety.

FIELD OF THE INVENTION

The present invention relates to transgenic nonhuman animals wherein the RGMc gene is altered, producing an animal lacking functional RGMc.

BACKGROUND OF THE INVENTION

Work in the chick visual system has suggested that the graded expression of Repulsive Guidance Molecule (RGM) gene product might play a role in the establishment of topographic projections in the developing visual system from the retina to the tectum (Monnier et al. (2002), Nature 419:392-395). It has also been demonstrated Niederkofler et al. (2004), J. Neuroscience 24:808-818) that in the mouse there are three proteins homologous to the chick RGM ("cRGM"). The mouse RGM (mRGM) family members were named mRGMa: Genbank Accession number AI118914; mRGMb: Genbank Accession number BG519283; mRGMc: Genbank Accession number AA656608. Gene targeting studies in the mouse have shown that mRGMa does not appear to be involved in anterior-posterior mapping of topographic projections from the retina to the superior colliculus in the mouse visual system (Niederkofler et al. (2004), J. Neuroscience 24:808-818). Human homologues for all three genes have also been found (Genbank Accession numbers: huRGMa: NM_020211; huRGMb: NM_173670; huRGMc: NM_213653). By gene linkage analysis, the human RGMc has recently been demonstrated to be HFE2 (Papanikolaou et al. (2004), Nat Genet. 36:77-82). Based on linkage analysis, a role for the RGMc/HFE2 gene in the regulation of iron metabolism in humans has recently been proposed (Papanikolaou et al. (2004), Nat Genet. 36:77-82). Tissue profile experiments demonstrated expression of mRGMc predominately in muscle, with highest levels in skeletal muscle, as well as heart and liver (Niederkofler et al. (2004), J. Neuroscience 24:808-818).

Human juvenile hemochromatosis is an early-onset, autosomal recessive disorder of iron metabolism resulting in increased iron absorption and storage. This iron overload has been associated with cardiomyopathy, diabetes and hypogonadism presenting in the teens and early 20s. Recently, mutation of HFE2 on chromosome 1q has been shown to cause this disease in humans (Papanikolaou et al. (2004), Nat Genet, 36:77-82). Human HFE2 encodes the protein hemojuvelin, which is orthologous to murine RGMc (>85% amino acid identity). Due to the involvement of the mRGMc/HFE2 gene in the onset of these conditions, the generation of RGMc modified transgenic animals would aid in defining the biological role(s) of RGMc/HFE2, and produce an animal model of RGMc/HFE2 deficiency to be used in the design and assessment of chemical and biological approaches to modulating RGMc/HFE2 activity. Such RGMc modified transgenic animals can also be used as a valuable source of cells for cell culture experiments as well as high-throughput screening assays at the cellular level.

SUMMARY OF THE INVENTION

A non-human animal that does not have functional RGMc has been generated and is disclosed herein. These animals provide a valuable animal model to understand the function of RGMc/HFE2 and to evaluate the therapeutic effects of drugs that modulate the function or the expression of the encoded protein in human cells. Moreover, these animals could provide important information on the mechanisms leading to iron accumulation in the body.

DETAILED DESCRIPTION OF THE INVENTION

Figure 1:
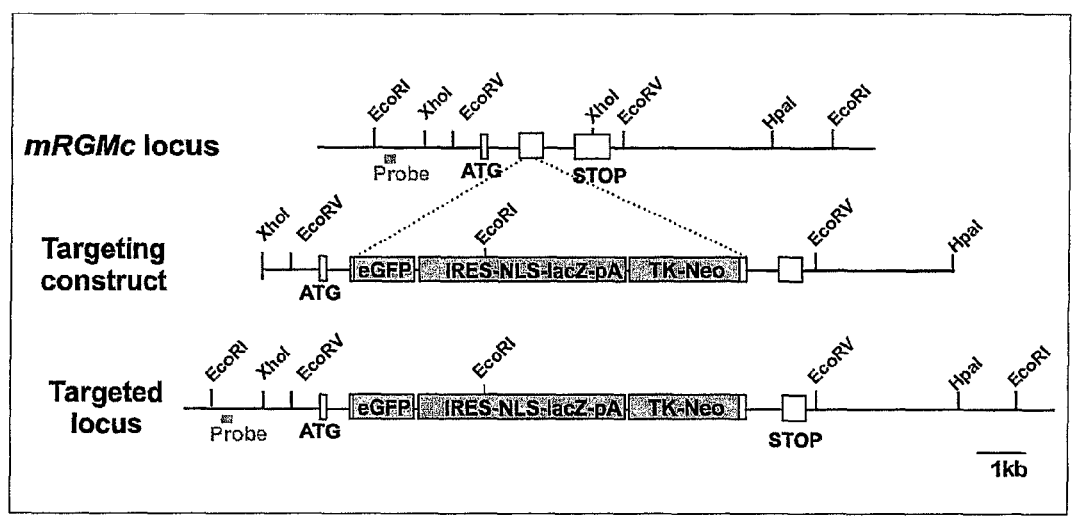
FIG. 1: Disruption of the mouse RGMc gene.
Map showing the organization of the mRGMc gene before (top) and after (bottom) homologous recombination with the targeting construct (middle). A mouse genomic library was screened using full-length mRGMc cDNA as a probe. The second coding exon of mRGMc was disrupted by inserting a cassette containing an eGFP gene, an IRES-NLS-LacZ-pA and a thymidine kinase (TK)-neomycin using homologous recombination in embryonic stem ("ES") cells (targeting frequency, ~1:100). An 11 kb DNA fragment from a genomic clone of the second coding exon of mRGMc containing an eGFP gene, an IRES-NLS-LacZ and a thymidine kinase (TK)-neomycin was used in the targeting construct as a homologous region for recombination. Cassettes for IRES-NLS-LacZ and herpes simplex thymidine kinase (TK)-neomycin have been described previously (Arber et al. (1999), Neuron 23:659-674; Niederkofler et al. (2004), J. Neuroscience 24:808-818) and eGFP cDNA was from Clontech (Catalog number 6081-1: pEGFP-N2). This cassette was cloned into Exon 2 in frame with the endogenous start codon (ATG) of mRGMc present on Exon 1.

RGMc expressed in mice contains an N-terminal consensus signal peptide for targeting to the endoplasmic reticulum and a C-terminal GPI anchor consensus sequence. COS cell transfections and chick electroporation studies confirm the localization of mRGMc at the plasma membrane. In addition to the proteolytic processing of the N-terminal signal peptide, mRGMc is cleaved once more (between amino acid 165 and amino acid 166) to yield two proteolytic fragments, an N-terminal fragment containing an integrin-binding RGD motif and a C-terminal GPI-anchored fragment (Niederkofler et al. (2004), J. Neuroscience 24:808-818). The predicted molecular weight of the C-terminal fragment is 24.8 kD, but the exact size in vivo is unknown. mRGMc protein is encoded by a single copy gene named the mRGMc gene. mRGMc is composed of three coding exons that are located within a 3 kb region on mouse chromosome 3 (chromosomal location: 3qF2.1), with each exon separated by approximately 500 bp. The mRGMc modified transgenic mice that we have generated provide a model in which the mRGMc gene was disrupted by homologous recombination ("HR").

The process of generating the knockout mice can be divided into 4 basic stages:
1. Cloning of the mRGMc gene and preparation of a DNA targeting construct for transfection of embryonic stem cells;
2. Isolating transfected ES cells in which the RGMc gene has been disrupted by HR on one of the two alleles;
3. Generating chimeric mice from mouse embryos injected with the successfully targeted ES cells; and
4. Breeding chimeric mice with wild-type mice to obtain heterozygous mice by germ line transmission and interbreeding of heterozygous mice to obtain knockout mice.

The present invention utilizes the mRGMc gene clone and the corresponding locus in the genome to generate transgenic animals in which the mRGMc gene has been made nonfunctional. The alterations to the naturally occurring gene can be modifications, deletions and substitutions. Modifications and deletions render the naturally occurring gene nonfunctional, producing a "knockout" animal. Substitution of the naturally occurring gene for a gene from a second species results in an animal which produces the gene product of the second species. Substitution of the naturally occurring gene for a gene having a mutation results in an animal which produces the mutated gene product. These transgenic animals are critical for therapeutic drug studies, the creation of animal models of human diseases, and for eventual treatment of disorders or diseases associated with human homologue of the RGM family as described herein and elsewhere. A transgenic animal carrying a disruption or "knockout" of the RGMc gene is useful for the establishment of a nonhuman model for diseases involving RGM equivalents such as HFE2 in the human.

The sequence of the mRGMc gene is known (Niederkofler et al. (2004), J. Neuroscience 24:808-818). The mRGMc genomic DNA is cloned from a mouse genomic library and is checked to make sure it has the expected characteristics of DNA encoding mRGMc protein. A transgenic mouse carrying the disrupted mRGMc gene is generated by homologous recombination of a target DNA construct with the endogenous gene on the chromosome. The transgenic mouse carrying the disrupted mRGMc gene does not express functional mRGMc molecules anymore, and is therefore useful in establishing an in vivo model for human disease, in particular diseases relating to iron metabolism and specifically HFE2-mediated diseases in iron metabolism.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at a sub-cellular level, such as by targeted recombination, microinjection or infection with recombinant virus. The term "transgenic animal" is not intended to encompass classical crossbreeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA. The term "germ-line transgenic animal" refers to a transgenic animal in which the genetic alteration or genetic information was introduced into germline cells, thereby conferring the ability to transfer the genetic information to its offspring. If such offspring in fact possess some or all of that alteration or genetic information, they are transgenic animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The non-functional RGMc gene generally should not fully encode the same RGMc native to the host animal, and its expression product should be altered to a minor or great degree, or absent altogether. However, it is conceivable that a more modestly modified RGMc will fall within the scope of the present invention.

The genes used for altering a target gene may be obtained by a wide variety of techniques that include, but are not limited to, isolation from genomic sources, preparation of cDNAs from isolated mRNA templates, direct synthesis, or a combination thereof.

A type of target cells for transgene introduction is the ES cells. ES cells may be obtained from pre-implantation embryos cultured in vitro and fused with embryos (Evans et al. (1981), Nature 292:154-156; Bradley et al. (1984), Nature 309:255-258; Gossler et al. (1986), Proc. Natl. Acad. Sci. USA 83:9065-9069; Robertson et al. (1986), Nature 322:445-448; Wood et al. (1993), Proc. Natl. Acad. Sci. USA 90:4582-4584). Transgenes can be efficiently introduced into the ES cells by standard techniques such as DNA transfection using electroporation or by retrovirus-mediated transduction. The resultant transformed ES cells can thereafter be combined with morulas by aggregation or injected into blastocysts from a non-human animal. The introduced ES cells thereafter colonize the embryo and contribute to the germline of the resulting chimeric animal (Jaenisch (1988), Science 240:1468-1474).

Since RGMc is an independent component of a complex mechanism, the proteins, including that encoded by the RGMc DNA, must be examined both individually and as a group if their contribution to the mechanisms of iron metabolism are to be understood. One approach to the problem of determining the contributions of individual genes and their expression products is to use isolated genes to selectively inactivate the native wild-type gene in totipotent ES cells (such as those described herein) and then generate transgenic mice. The use of gene-targeted ES cells in the generation of gene-targeted transgenic mice was described 1987 (Thomas et al. (1987), Cell 51:503-512) and is reviewed elsewhere (Frohman et al. (1989), Cell 56:145-447; Capecchi (1989), Trends in Genet. 5:70-76; Baribault et al. (1989), Mol. Biol. Med. 6:481-492; Wagner (1990), EMBO J. 9:3025-3032; Bradley et al. (1992), Bio/Technology 10:534-539).

Techniques are available to inactivate or alter any genetic region to any mutation desired by using targeted homologous recombination to insert specific changes into chromosomal alleles.

As used herein, a "targeted gene" is a DNA sequence introduced into the germline of a non-human animal by way of human intervention, including but not limited to, the methods described herein. The targeted genes of the invention include DNA sequences which are designed to specifically alter cognate endogenous alleles.

Deleterious mutations of the HFE2 gene product, hemojuvelin, (Pietrangelo (2004), N Engl J Med. 350:2383-2397) result in iron accumulation in various tissues (liver, pancreas, heart). Hepcidin (Pietrangelo (2004), N Engl J Med. 350: 2383-2397), a small peptide produced by the liver, and a negative regulator of iron absorption is greatly reduced in cases of hemojuvelin mutation in humans. mRGMc mutant mice display similar features to human juvenile hemochromatosis patients. mRGMc mutant mice show iron overload beginning at postnatal stages as well as strongly reduced hepcidin expression. Reduction in reticuloendothelial iron storage, another indicator of juvenile hemochromatosis is also observed in mRGMc mutant mice. These findings demonstrate that RGMc mutant mice are a valuable tool to study molecular and cellular mechanisms of juvenile hemochromatosis. Moreover, these mice should also provide a powerful animal model for pharmacological interventions aiming at ameliorating this disease in humans.

Different HFE2 mutations have been mapped in the human (Papanikolaou et al. (2004), Nat Genet. 36:77-82) and shown to be spread throughout the molecule. Moreover, several of these point mutations represent point mutations without creating premature truncation of the protein. It therefore seems likely, that mutation could influence trafficking of RGMc/HFE2 to the cell surface and drugs which might enhance cell surface accumulation of mutant RGMc/HFE2 forms would represent a useful therapeutic agent. Moreover, mRGMc knockout mice are useful to demonstrate the in vivo function of mRGMc/HFE2 and the effects of therapeutic intervention of pathways of iron metabolism working through mRGMc/HFE2.

mRGMc knockout mice will help to define the role of RGMc/HFE2 and an interaction with hepcidin as well as all other proteins involved in the iron metabolism pathway in which RGMc act for animal development, maturation and disease. In the mRGMc knockout mice, postnatal accumulation of iron is observed in the liver where mRGMc is expressed in a subpopulation of cells. It is thus likely the expression of RGMc in the liver is the cause of the rapid progression of this disease. Moreover, the absence of RGMc in mutant animals causes a massive reduction in hepcidin, a secretory peptide which has been implicated in the regulation of iron uptake previously through mouse genetic experiments (Pietrangelo (2004), N Engl J Med. 350:2383-2397). mRGMc mutant mice appear normal at birth and also in adulthood cannot obviously be phenotypically distinguished from their littermates. mRGMc mutant mice do however, have a noticeable discoloration of liver and pancreatic tissue, not present in wildtype and heterozygous littermates which is visible by eye by 6 weeks of age.

Future studies will address the exact position of RGMc in the iron metabolism pathway and the mechanism of action of RGMc mutation upon this pathway, as it occurs naturally in the disease. It will be determined whether these mutations cause protein trafficking defects, and how RGMc expression in the liver is involved in regulating iron levels and hepcidin expression in liver hepatocytes.

The effect of RGMc/HFE2 on the progression of juvenile hemochromatosis will also be studied in mRGMc knockout mice. Juvenile hemochromatosis is an early-onset autosomal recessive disorder of iron overload resulting in cardiomyopathy, diabetes and hypogonadism that presents in the teens and early 20s (Pietrangelo (2004), N Engl J Med. 350:2383-2397; Hentze et al. (2004), Cell 117:285-297). Juvenile hemochromatosis has previously been linked to the centromeric region of chromosome 1q (Papanikolaou et al. (2004), Nat Genet. 36:77-82), a region that is incomplete in the human genome assembly. The positional cloning of the locus associated with juvenile hemochromatosis and the identification of the HFE2 gene as crucial to iron metabolism has been reported (Papanikolaou et al. (2004), Nat Genet. 36:77-82). The recombinant interval has been mapped in families of Greek, Canadian and French descent and identified multiple deleterious mutations in a transcription unit of previously unknown function (LOC148738), now called HFE2, whose protein product is called hemojuvelin has been identified. Analysis of afflicted families indicated that one mutation, the amino acid substitution G320V, was observed in all three populations and accounted for two-thirds of the mutations found. HFE2 transcript expression was restricted to liver, heart and skeletal muscle, similar to that of hepcidin, a key protein implicated in iron metabolism. Urinary hepcidin levels were depressed in individuals with juvenile hemochromatosis, suggesting that hemojuvelin is probably not the hepcidin receptor. Rather, HFE2 seems to modulate hepcidin expression.

Cells isolated from mRGMc knockout mice may be used to study the precise cellular location of defects in iron metabolism when compared to wild-type cells, to study consequences of transfection with mutated RGMc/HFE2 forms isolated from humans to study which mutations lead to protein trafficking defects in mutant cells and to perform high-throughput screens to test drugs which might influence expression of RGMc/HFE2 or trafficking of RGMc/HFE2 to the cell surface.

The following Examples are presented for the purpose of illustrating the present invention and are not to be construed as a limitation on the scope of this invention.

EXAMPLE 1

Isolation of the Mouse RGMc Genomic Clones

To disrupt a specific gene by homologous recombination, DNA constructs containing the genomic region of the disrupted gene are needed for electroporation of ES cells. To obtain these a genomic mouse library was screened by Incyte Genomics (Palo Alto, Calif.) using full-length mRGMc cDNA as probe (agarose gel eluted unlabelled fragment (Qiagen Gel Extraction Kit (Cat. No. 28706). The obtained BAC clone (Incyte Genomics no. 26773) was used to subclone an approximately 10 kb genomic region (EcoRI-EcoRI) (FIG. 1) containing all 3 coding exons of mRGMc.

EXAMPLE 2

Preparation of Gene-targeting Constructs

A 8 kb fragment (XhoI-HpaI) of the above described 10 kb EcoRI-EcoRI clone was sub-cloned in into a modified pBluescript SK+ plasmid containing a PmeI restriction site for linearization (pBluescript SK+: Stratagem 212205). An eGFP-IRES-NLS-lacZ-neo cassette (cassettes for IRES-NLS-LacZ and herpes simplex thymidine kinase (TK)-neomycin have been described previously (Arber et al. (1999), Neuron 23:659-674; Niederkofler et al. (2004), J. Neuroscience 24:808-818) and eGFP cDNA was from Clontech (Catalog number 6081-1: pEGFP-N2)) was inserted into the modified exon 2 in frame with the endogenous start codon (ATG) of mRGMc present on exon 1. This modification (performed by PCR) deleted the majority of exon 2 (except for the splice acceptor and donor sites). This final construct was electroporated into ES-cells and selected for neomycin resistance as described below.

EXAMPLE 3

Isolation of Gene-targeted ES Cell Lines: Transfection of ES Cells

The DNA construct was linearized (50-60 µg) conserving vector sequences next to the TK gene to protect it from nuclease digestion after electroporation. 30 µg of linearized DNA are needed for one electroporation. After linearization, the protruding ends of the DNA fragment were blocked by reaction with ddNTPs (Pharmacia, No. 27-2054). DNA was then precipitated by a single phenol/chloroform/isoamylalcohol extraction followed by two chloroform/isoamylalcohol extractions and the whole digest was applied to a preparative gel. The DNA agarose band containing the linearized fragment was electroeluted with the Elutrap apparatus. The DNA was then precipitated and taken up in a very small volume of sterile $ddH_2O$ (final concentration 1-2 µg/ul).

E14 ES cells (129 Ola; Niederkofler et al. (2004), J. Neuroscience 24:808-818) were maintained at an undifferentiated stage by co-culturing with mouse embryonic fibroblasts ("feeder cells") inactivated by mitomycin (Hogan et al. (1989), Manipulating the Mouse Embryo—A Lab. Manual. Cold Spring Harbor Lab. Press, Cold Spring Harbor, N.Y. 11724, USA, pp 371). Feeder cells were prepared from E14 embryos of a transgenic cell line expressing neomycin (Hogan et al. (1989), Manipulating the Mouse Embryo—A Lab. Manual. Cold Spring Harbor Lab. Press, Cold Spring Harbor, N.Y. 11724, USA, pp 386).

For DNA transfection, ES cells (dish of 10 cm diameter) were harvested by trypsin treatment and resuspended in 800 µl of culture medium at a concentration of $10^7$. 30 µg of linearized DNA (in about 30 µl) was added to the ES cell suspension for electroporation using the Gene Pulser (Bio-Rad) and Capacitance Extender at capacitance 500 µFD, 250 V, time constant between 6.6 to 7.5. Thereafter, the cells were incubated for 10 minutes at room temperature.

Transfected ES cells were plated onto feeder cell coated 10×10 cm plates in culture medium. The next day the medium was changed. Two days after transfection cells were subject to neomycin drug selection in medium containing 200 µg/ml final concentration G418 (GIBCO) and LIF at a dilution of 1:10000. Recombinant LIF is called ESGRO, from Chemicon International Catalog number ESG1107. Thereafter selection was maintained and the medium was changed every day. The first clones are visible 7 days after the electrophoretic transfection.

Screening for Homologous Recombination in ES Cells

The size of ES colonies on day 10 after transfection was large enough to transfer individual clones to 24-well plates. To collect and transfer a clone of ES cells; cells were picked up by aspiration onto a cone attached to a Pipetman (set at 80 µl) and transferred to a 96 well plate containing 100 µl of trypsin (from 1× stock). The ES clone was resuspended by pipetting 5 or 6 times up and down. The cell suspension was then transferred to a 24 well plate again co-cultured with mouse embryonic fibroblasts. After approximately 5 days in culture during which the medium was changed daily, individual ES cell clones were treated with trypsin-EDTA (as above) (Gibco Catalog number: 25300-O54). After trypsin treatment a portion of the cells was used to confirm mRGMc knockout.

ES cell recombinants were screened for homologous recombination events by genomic Southern blot analysis according to established procedures outlined in the Digoxigenin DNA labeling kit (Roche Catalog number 1175033) for Southern blot analysis. 10 µg of genomic DNA isolated from ES cells was digested using EcoRI. The probe for Southern blots was made by PCR using the following primers: 5'-ctc agt gta tta tgt gta gaa-3' and 5'-aat tcc agg aac gtt ggt ggc-3') according to the instructions of the above kit (Roche Catalog number 1175033). Location of the probe used in Southern blot hybridization is shown in FIG. 1.

Confirmation of Gene-targeted ES Cells by Genomic Southern Hybridization

Genomic DNA was digested with EcoRI, resolved on a 1% agarose gel, blotted onto positively charged nylon membrane (Roche; Catalog number 1209272), and hybridized to a digoxigenin-labeled DNA probe. The ~300 bp digoxigenin-labeled probe (generated by PCR) hybridized to a 10 kb fragment in the wildtype mRGMc gene and to a 4.5 kb band in the mRGMc gene that had undergone homologous recombination with the targeting construct. The genomic locus, the targeting construct and the targeted locus are shown in FIG. 1. Genomic DNA was digested with EcoRI, resolved on a 1% agarose gel, blotted onto positively charged nylon membrane (Roche; Catalog number 1209272), and hybridized to a digoxigenin-labeled DNA probe.

EXAMPLE 4

Aggregation of the Gene-targeted ES Clone with Zona-free Embryos

ES cells carrying the desired genotype were co-cultured with denuded post-compacted eight-cell stage mouse embryos (Wood et al. (1993), Proc. Natl. Acad. Sci. USA 90:4582-4585). Eight-cell embryos from ([C57BL/6×BalbC] F1 females×C57BL/6 males) at a post-compaction stage are placed in M2 medium (Hogan et al. (1989), Manipulating the Mouse Embryo—A Lab. Manual. Cold Spring Harbor Lab. Press, Cold Spring Harbor, N.Y. 11724, USA). Batches of 20 embryos are briefly incubated in acidified Tyrodes solution (Hogan et al. (1989) supra) until dissolution of their zona pellucida. Meanwhile, ES cells are trypsinised to obtain a single cell suspension and resuspended at a concentration of $10^6$ cells/ml in co-culture medium (Wood et al. (1993), Proc. Natl. Acad. Sci. USA 90:4582-4585). Ten zona-free embryos are placed in 50 µl droplets of the ES cell suspension and incubated at 37° C. for 2-3 hours to allow random aggregation of ES cells with post-compaction embryos. Embryos are allowed to recover and develop overnight in M16 medium (Hogan et al. (1989), Manipulating the Mouse Embryo—A Lab. Manual. Cold Spring Harbor Lab. Press, Cold Spring Harbor, N.Y. 11724, USA), and finally they were transferred into pseudo-pregnant foster mothers [(C57BL/6×BalbC) F1 females×vasectomised males.

EXAMPLE 5

Breeding Chimeric Mice

The chimeric male mice were bred to wild-type C57BL/6 (black coated) female mice. Some of the progeny from the chimera X C57BL/6 cross are expected to be agouti with white belly if the chimeric male had ES cell genetic material incorporated into its germ line (agouti is dominant to black coat color). These crosses are performed to test for the transfer of ES cell genetic information, including the disrupted mRGMc gene, to its offspring.

To determine the mRGMc genotypes, genomic DNA was purified from about 1 cm of tail from each mouse after weaning. The genomic DNA was isolated by digestion with Proteinase K, followed by phenol and phenol:chloroform extractions and ethanol precipitation. Southern blot hybridization analysis was used to identify offspring which contained the disrupted mRGMc gene. The identification of mRGMc mutant mice after germline transmission of the mutant allele was performed both by genomic Southern blotting and PCR. For Southern blotting, 10 µg of genomic DNA isolated from wildtype (+/+), heterozygous (+/−), and homozygous (−/−) mice were used for the analysis, using the same strategy as for ES cells (see above). Primers used for PCR screening were as follows: 5'-cca gtg caa gat cct ccg ctg c-3' and 5'-tcc gga tgg tgg tag cgt tgg c-3'. These transgenic offspring are heterozygous for the mRGMc gene disruption. Both transgenic heterozygous and nontransgenic mouse (tail) genomic DNAs were digested with EcoRI, resolved on a 1% agarose gel, blotted onto positively charged nylon membrane (Roche; Catalog number 1209272), and hybridized to a digoxigenin-labeled DNA probe as shown in FIG. 1 to confirm the mutant mRGMc gene structure. Southern hybridization analysis confirmed that the structure of the altered mRGMc gene was identical to that predicted, and previously characterized in the mRGMc-targeted ES clones.

EXAMPLE 6

Breeding Heterozygous Mice and Generation of Homozygous mRGMc Deficient Mice

Male and female transgenic mice, each of which contained one copy of the altered mRGMc gene (heterozygous mice), were mated with each other to generate mice in which both copies of the mRGMc gene are the targeted, altered transgenic mRGMc gene. It was predicted that one fourth of the mouse embryos would be homozygous for the altered mRGMc gene. Surviving offspring are genotyped by Southern hybridization analysis as described above. Homozygous mutant mice are born at a ratio of 1 in 4 pups if the defective gene does not affect embryo development in any obvious way by visual inspection of the embryos. Homozygous mutant mice are identified by analysis of tail DNA samples, as described above.

EXAMPLE 7

Characterization of Homozygous mRGMc Deficient Mice

Figure 2:
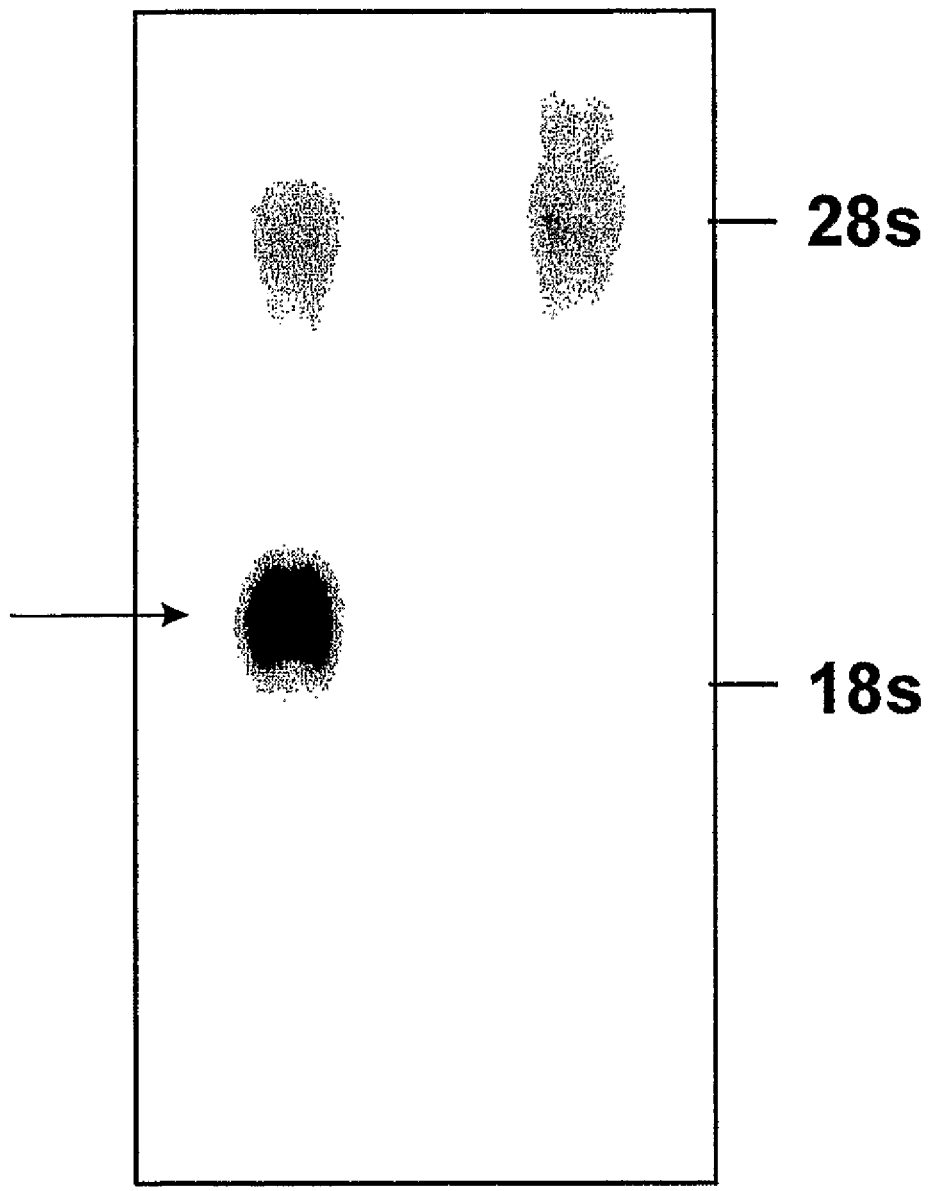
FIG. 2: Expression of mRGMc in muscle tissue of mRGMc$^{-/-}$ and mRGMc$^{+/+}$ (WT) by Northern blot analysis.
Northern blot analysis (Niederkofler et al. (2004), J. Neuroscience 24:808-818) using digoxigenin-labelled RNA probes to mRGMc confirmed the complete absence of mRGMc mRNA in total RNA isolated from muscles of mRGMc$^{-/-}$ mutant animals (P21 HL: postnatal day 21 hindlimb muscles; size of mRGMc message is shown by arrow). These findings demonstrate that no mRGMc message is made by these mice. Therefore, they represent full mutant mice as they can no longer produce any mRGMc protein.
Figure 3:
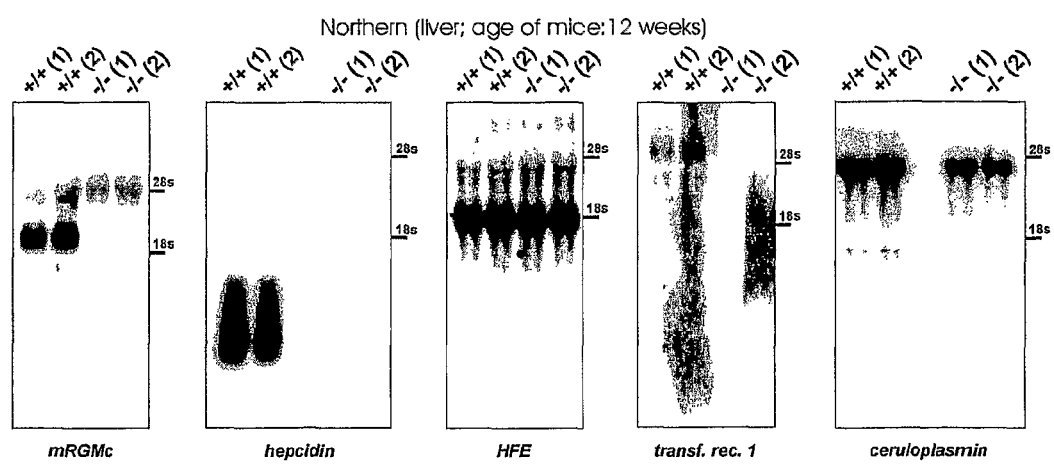
FIG. 3: Northern blot of genes known to be involved in iron metabolism.
Northern blots (Niederkofler et al. (2004), J. Neuroscience 24:808-818) comparing wildtype livers with mRGMc mutant livers of 12 week old mice, mRGMc is absent in mRGMc mutant mice. Hepcidin (GenBank Accession No. BC021587) is massively downregulated. HFE (GenBank Accession No. AA255260) and ceruloplasmin (GenBank Accession No. AI225600) are unchanged. Transferrin receptor 1 (GenBank Accession No. BC054522) is downregulated.
Figure 4:
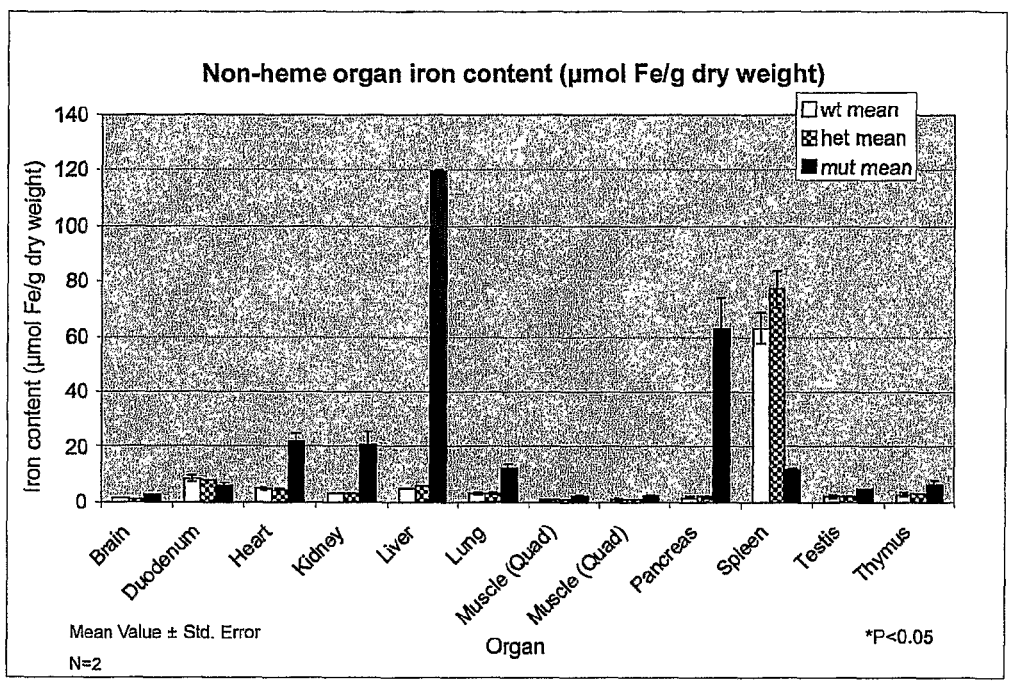
FIG. 4: Iron distribution in mRGMc$^{-/-}$, mRGMc$^{+/-}$ and mRGMc$^{+/+}$ mice.
Non-heme iron was quantitatively measured according to the method of Torrance and Bothwell (Methods Hematol. 1:90-115, 1980). At ten weeks of age mRGMc$^{-/-}$ animals show massive increases of iron stored in various organs. Liver iron is increased 25-fold while pancreas, heart, kidney, brain, testis and lung also show significant increases in iron accumulation. Splenic iron is greatly reduced in mRGMc$^{-/-}$ mutant animals (*P<0.05, students t-test), mRGMc$^{+/-}$ animals show iron storage indistinguishable from their wildtype littermates.

Northern blot analysis of 12 week old mRGMc mutant mice demonstrated complete ablation of mRGMc expression in liver (FIG. 3) and muscle tissue (FIG. 2). These mutants have increased iron storage in liver, heart and pancreas and decreased iron storage in the spleen compared to wild type controls, as demonstrated by Perls Prussian Blue staining, (FIG. 4). Further, mRGMc$^{-/-}$ mice have elevated ferritin and serum iron levels compared to WT. mRGMc$^{-/-}$ mutant mice were also demonstrated to be hepcidin deficient (FIG. 3).

The invention claimed is:

1. A transgenic mouse whose genome comprises a homozygous disruption of the endogenous repulsive guidance molecule c ("RGMc") gene, wherein expression of the endogenous RGMc gene is abrogated or reduced, and wherein the mouse exhibits, relative to a wild-type mouse, a phenotype that is characterized by increased iron storage in liver, increased iron storage in heart, increased iron storage in pancreas and decreased iron storage in spleen.

2. A method of producing the transgenic mouse of claim 1 comprising:
   (a) introducing a gene encoding a disrupted form of RGMc designed to target the RGMc gene by homologous recombination into mouse embryonic stem cells;
   (b) injecting the embryonic stem cells containing the disrupted RGMc gene into mouse blastocysts;
   (c) transplanting the injected blastocysts into a pseudopregnant foster mother; and
   (d) allowing the embryo to develop producing a founder transgenic mouse.

3. The method of claim 2 wherein the introducing of step (a) is by electroporation.

* * * * *